(12) United States Patent
Koblanski

(10) Patent No.: US 6,517,492 B2
(45) Date of Patent: Feb. 11, 2003

(54) METHOD AND APPARATUS FOR ASSESSMENT OF CARDIAC FUNCTION BY MONITORING MOVEMENT OF THE TRACHEA

(75) Inventor: John Koblanski, Burnaby (CA)

(73) Assignee: Texon Technologies Ltd., Vancouver (CA)

(*) Notice: Subject to any disclaimer, the term of this patent is extended or adjusted under 35 U.S.C. 154(b) by 0 days.

(21) Appl. No.: 09/791,518

(22) Filed: Feb. 22, 2001

(65) Prior Publication Data
US 2002/0115936 A1 Aug. 22, 2002

(51) Int. Cl.⁷ ................................................ A61B 5/02
(52) U.S. Cl. .......................................... 600/481; 600/508
(58) Field of Search ........................... 600/481, 485, 600/486, 500, 508, 300

(56) References Cited

U.S. PATENT DOCUMENTS

| | | | |
|---|---|---|---|
| 3,593,703 A | | 7/1971 | Gunn et al. .................. 128/2 R |
| 4,383,534 A | | 5/1983 | Peters |
| 4,530,354 A | | 7/1985 | Froilan |
| 4,967,759 A | * | 11/1990 | Teves .......................... 600/528 |
| 4,993,420 A | | 2/1991 | Welkowitz et al. .......... 128/668 |
| 5,033,472 A | | 7/1991 | Sato et al. ................... 128/691 |
| 5,080,107 A | * | 1/1992 | Teves .................... 128/207.15 |
| 5,263,478 A | | 11/1993 | Davis |
| 5,293,874 A | | 3/1994 | Takahashi et al. ........... 128/687 |
| 5,445,144 A | * | 8/1995 | Wodicka et al. ........ 128/207.14 |
| 5,865,759 A | | 2/1999 | Koblanski ................... 600/508 |
| 5,964,223 A | | 10/1999 | Baran |
| 6,171,258 B1 | | 1/2001 | Karakasoglu et al. |
| 6,292,689 B1 | * | 9/2001 | Wallace et al. .............. 600/547 |

FOREIGN PATENT DOCUMENTS

| | | |
|---|---|---|
| EP | 0 357 275 | 3/1990 |
| EP | 0 444 594 | 9/1991 |
| EP | 0 764 842 | 3/1997 |
| FR | 2 672 794 | 8/1992 |

OTHER PUBLICATIONS

XP–002072289, Tavel, "Clinical Phonocardiography and External Pulse Recording", Year Book Medical Publishers, Inc., 1978.
Tavel, "Ejection Sound (Ejection Click)", Clinical Phonocardiography and External Pulse Recording, 3rd Edition, 1978, pp. 75–78.
Tavel, "Normal Sounds and Pulses: Relationships and Intervals Between the Various Events", Clinical Phonocardiography and External Pulse Recording, 4th Edition, 1978, pp. 39–45.
Benchimol, "Ultrasound", Non–Invasive Diagnostic Techniques In Cardiology, 1977, pp. 15–38.
Rushmer, "Ballistocardiography", Chapter 3, The Cardiac Output, pp. 91–97, "The Mechanical Effects Of Cardiac Contraction", Chapter 2, Functional Anatomy of Cardiac Contraction, pp. 50–52, Cardiovascular Dynamics, 2nd Edition, 1961.

(List continued on next page.)

*Primary Examiner*—Kevin Shaver
*Assistant Examiner*—Navin Natnithithadha
(74) *Attorney, Agent, or Firm*—Christie, Parker & Hale, LLP (57) ABSTRACT

A method and apparatus to assess cardiac function in a subject involves supporting a probe in the trachea for transmitting movement of the trachea in response to heart function. The transmitted movement is detected by a sensor which generates a waveform signal. The waveform signal is displayed and assessed to determine cardiac function. By directly engaging the trachea, the apparatus and method of the present invention are sensitive to very small accelerations, velocities or displacements of the trachea to permit accurate measurement of cardiac function.

49 Claims, 9 Drawing Sheets

OTHER PUBLICATIONS

Morton E. Tavel, "Clinical Phonocardiography and External Pulse recording," 1978 Yearbook, Medical Publishing Inc. (On Order).

Alberto Benchimol, "Non–Invasive Diagnostic Techniques in Cardiology, " 1977, The Williams and Wilkins Co. (On Order).

Robert F. Rushmer, "Cardiovascular Dynamics," 1961, W. B. Saunders Company (On Order).

Rushmer, Circulation—vol. 29: 268–283, 1964 (On Order).

* cited by examiner

METHOD AND APPARATUS FOR ASSESSMENT OF CARDIAC FUNCTION BY MONITORING MOVEMENT OF THE TRACHEA

FIELD OF THE INVENTION

This invention relates to an apparatus and method to assess cardiac function in a subject.

BACKGROUND OF THE INVENTION

Non-invasive methods of determining cardiac functioning include the following:
  a) Mechanical methods that include pulse recording of the jugular, carotid artery or apexcardiogram. This group also includes sound recordings, for example, use of the stethoscope and phonocardiographic techniques.
  b) Electrical techniques which are best exemplified by the electrocardiogram (ECG).
  c) Relatively more recent techniques include imaging techniques, for example echocardiography, nuclear cardiography, radiographic techniques and magnetic resonance imaging (MRI).

All of the above the mechanical methods, which rely on vibration and sound recording, involve measuring the movements of the body resulting from cardiac activity. This means that the mass of the body is part of the recording means. This is not desirable. Chest movements, for example, are dependent upon chest shape, and sound recording is dependent upon the amount of fat and the condition of the lung tissue for its amplitude. An accurate trace pattern is difficult to achieve and these techniques are therefore of limited diagnostic value.

Electrical methods measure only the electrical field generated by the heart. This cannot provide a direct measure of the cardiac forces generated by the heart and therefore these methods are incapable of evaluating the heart's function as a pump.

Imaging techniques have limited ability to evaluate the force of the heart's contraction.

Thus none of the above methods is capable of measuring the force of the heart's contraction. As a result the evaluation of the condition of the myocardium is not possible. Heart attack risk cannot be determined by any known non-invasive method. A patient may be diagnosed as normal and yet die of a heart attack shortly after the diagnosis.

Relevant literature includes the following text books: Clinical Phonocardiography and External Pulse recording by Morton E. Tavel, 1978 Yearbook, Medical Publishing Inc.; Non-Invasive Diagnostic Techniques in Cardiology by Alberto Benchimol, 1977, The Williams and Wilkins Co.; and Cardiovascular Dynamics by Robert F. Rushmer, 1961, W.B. Saunders Company.

Rushmer first postulated that acceleration and deceleration of the various structures of the heart and blood explain heart sounds as well as their modifications with changing dynamic conditions. As acceleration is a function of force, the aortic blood acceleration is a manifestation of the force that sets the cardiac structures in motion. Other forces originate from the pressure gradient between the aorta and the left ventricle, which acts over the closed semilunar valve. The valve behaves like a circular, stretched membrane in which the thin, flexible leaflets can be stretched in all directions by the differential aorta—ventricular pressure. The energy of the rapid ejection phase of the left ventricle expands the aorta and the stored energy is in direct relationship to its wall elasticity. Measurement of the amplitude of the wave created after the maximum ejection rate, is a measure of the elasticity of the wall of the aorta. The elasticity of the aortic valve can also be measured by measuring the amplitude of the wave created after the valve is closed. The most sensitive indicators of performance are the rates of change of momentum as indicated by changes in velocity of the blood and heart mass. This acceleration is directly indicative of myocardial contractility which is one of the most difficult parameters to measure. In 1964 Rushmer established a direct relationship between the initial ventricular impulse and the peak flow acceleration during the systolic ejection—see Circulation—Volume 29: 268–283 1964.

Commonly owned U.S. Pat. No. 5,865,759 discloses a method and apparatus for measuring cardiac function using an external sensor positioned against the thyroid cartilage in the neck. The subject matter of U.S. Pat. No. 5,865,759 is incorporated herein by reference. The sensor detects the response of the thyroid cartilage to heart function and generates a signal that is fed to a signal processing unit to generate a waveform signal characteristic of heart function for assessment by a user. The apparatus and method of U.S. Pat. No. 5,865,759 provide reliable, accurate and inexpensive assessment of cardiac function.

SUMMARY OF THE INVENTION

The present invention provides an improved apparatus and method for assessment of cardiac activity by directly measuring the movement of the trachea. The apparatus and method rely on introduction of a sensing apparatus into the throat of the user to engage with the trachea. This arrangement is sensitive to very small movement forces and permits accurate measurement of cardiac function with even finer details.

Accordingly, the present invention provides apparatus to assess cardiac function in a subject comprising:
  a probe insertable and supportable in the trachea to transmit movement of the trachea in response to cardiac function through the probe;
  a sensor to detect the transmitted movement of the trachea and generate a signal indicative of the movement of the trachea; and
  a signal processing unit to receive the signal from the sensor and generate a waveform signal characteristic of the cardiac function.

The probe can be a hollow tube having an internal passage to deliver air to the subject and whereby movement of the hollow tube serves to transmit the movement of the trachea.

Alternatively, the apparatus can employ an endotracheal tube for housing the probe in which case the probe comprises a tubular member having an inner end adapted to protrude from the endotracheal tube and engage against the carina region at which the trachea bifurcates into the lungs.

The present invention also provides apparatus to assess cardiac function in a subject comprising:
  a tube insertable into the mouth of a subject such that a first end extends into the trachea and a second end protrudes from the mouth;
  a flexible support extendable from the tube to engage the trachea and suspend the tube within the trachea for movement of the tube along the longitudinal axis of the tube;
  a rigid anchor extendable from the tube to engage the trachea and transmit movement of the trachea due to cardiac function to the tube;

a sensor to sense the movement of the tube and generate a signal indicative of the movement of the trachea; and a signal processing unit to receive the signal from the sensor and generate a waveform signal characteristic of the cardiac function.

In a still further aspect, the present invention provides a method of assessing cardiac function in a subject comprising:

supporting a probe in the trachea to transmit movement of the trachea in response to cardiac function;

sensing the movement transmitted by the probe;

generating and displaying a waveform signal based on movement transmitted by the probe; and assessing the waveform signal to determine cardiac function.

The apparatus and method of the present invention are intended to be used primarily with human patients, however, the subject matter also finds application with animal subjects. The apparatus and method can be used with a conscious subject or when the subject is anaesthetised, for example, during surgery.

BRIEF DESCRIPTION OF THE DRAWINGS

Aspects of the present invention are illustrated, merely by way of example, in the accompanying drawings.

DESCRIPTION OF THE PREFERRED EMBODIMENTS

The apparatus and method of the present invention are directed to a new system for assessing cardiac function in a subject. Essentially, the apparatus of the present invention comprises a probe 4 insertable and supportable in the trachea of a subject to transmit movement of the trachea due to cardiac function. The transmitted movement of the trachea is detected by a sensor which generates a signal indicative of the trachea movement. This signal is passed to a signal processing unit which generates a waveform signal characteristic of the cardiac function. Details of the processing of the signal are disclosed in commonly owned U.S. Pat. No. 5,865,759 which also discloses externally monitoring the movement of the thyroid cartilage in order to monitor heart function. The present invention is directed to a n improved system which relies on internal monitoring of the movement of the trachea to provide an even more accurate picture of the heart function. The trachea is the passage reinforced by rings of cartilage through which air reaches the bronchial tubes from the larynx.

FIGS. 1–3b illustrate a first embodiment of the apparatus of the present invention in which the probe is a hollow tube 4 insertable through the mouth and throat of a user into the trachea and supportable therein. Movement of the tube itself serves to transmit the movement of the trachea.

Figure 1:
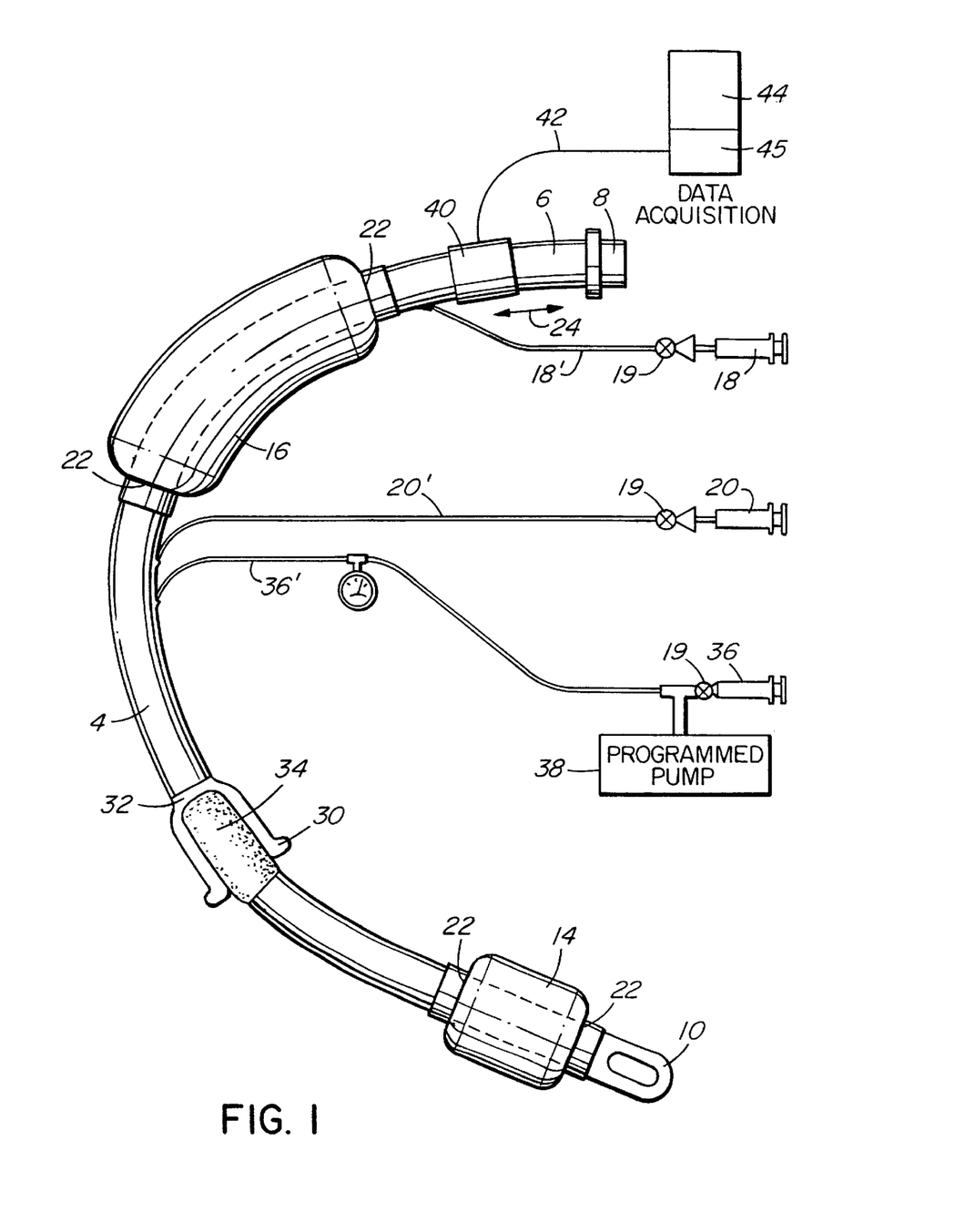
FIG. 1 is a schematic view of a first embodiment of the apparatus of the present invention which relies on movement of a tube within the trachea to transmit movement of the trachea due to cardiac function.

Referring to FIG. 1, hollow tube 4 has a structure similar to a conventional intubation device in that there is a hollow interior 6 that extends between an outer end 8 and an inner end 10 formed with a structure known as a Murphy Eye which ensures that the inner end does not become blocked. Tube 4 is insertable into the mouth of a subject such that inner end 10 extends into the trachea and outer end 8 protrudes from the mouth. Outer end 8 includes an attachment for ready connection to a ventilator unit (not shown) which can deliver air through tube interior 6 to inner end 10 and the trachea to allow a subject to breathe while the tube is in place.

A flexible support in the form of inflatable cuffs 14 and 16 are extendable from the tube to engage the anatomy of the subject and suspend tube 4 within the trachea for longitudinal movement. Lower cuff 14 is positioned to engage with the trachea. Upper cuff 16 is positioned within the mouth of the subject to prevent opposition to tube motion by mouth structures such as the teeth or tongue Cuffs 14 and 16 are shown in their inflated state in FIG. 1 extending radially outwardly from tube 4. As with a conventional intubation device, the side walls of tube 4 include sealed embedded air passages to permit inflation and deflation of cuffs 14 and 16. A separate syringe 18 or 20 is connected via line 18' or 20', respectively, to embedded air passages for independent control of each cuff. Syringes 18 and 20 include a check valve 19 to ensure that the cuffs remain inflated. Cuffs 14 and 16 are formed from soft, pliable plastic and dimensioned to be inflatable to a diameter that securely engages with the walls of the trachea or the mouth of the subject to reliably suspend tube 4 in place within the trachea. Two spaced cuffs 14 and 16 are shown supporting each end of tube in FIG. 1, however, it will be readily apparent to a person skilled in the art that additional cuffs may used intermediate the ends of the tube.

Cuffs 14 and 16 are sealably mounted to the external surface of tube 4 by annular end walls 22 that extend generally radially from the external surface. Transverse flexing of end walls 22 permits longitudinal movement of tube 4 in the direction indicated by arrow 24 within the trachea. On deflation, cuffs 14 and 16 collapse against external surface of tube 4 to permit ready insertion or removal of tube 4 from the trachea and mouth of the subject.

Figure 2A:
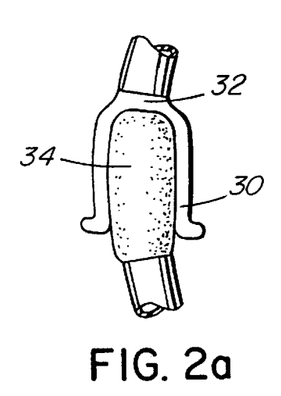
FIG. 2a is a detail view of the anchor for coupling the tube to the trachea in the folded position.
Figure 2B:
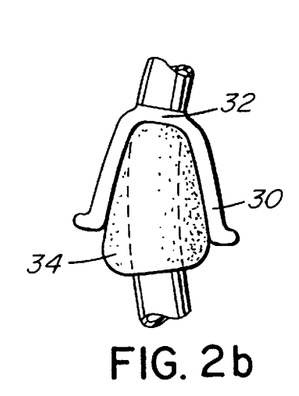
FIG. 2b is a detail view of the anchor in the expanded position.

In order to ensure that tube 4 moves with the trachea in response to cardiac function, tube 4 also includes a rigid anchor in the form of at least two hinged flanges 30 that are extendable radially outwardly from the external surface of tube 4 to engage the trachea. Each flange 30 is pivotally connected via a hinge joint to collar 32 which encircles tube 4. Preferably, an inflatable bladder 34 is provided inside flanges 30 between the flanges and tube 4. Bladder 34 acts to pivot the flanges between a folded position against the tube and a radially expanded position extending between the tube and the trachea. FIG. 1 and FIG. 2a show flanges 30 in the folded position in which the flanges lie substantially flat against the side of tube 4. FIG. 2b shows the flanges in the radially expanded position due to inflation of bladder 34. When in the expanded position, flanges 30, which are preferably formed from a rigid plastic, engage against the walls of the trachea to anchor tube 4 to the trachea such that tube 4 moves with the trachea. Tube 4 is supported by cuffs 14 and 16 within the trachea for longitudinal movement so that any movement of the trachea due to beating of the heart is transmitted by flanges 30 to tube 4. Inflation of cuff 34 is controlled manually by syringe 36 via line 36' (FIG. 1). A check valve 19 is also provided. Alternatively, a small air pump 38 can be programmed under computer control to vary pressure in bladder 34 so that the pressure is increased to a predetermined value for a period and reduced to a different pressure for another period. Operating in this manner prevents tissue necrosis in the trachea due to pressure of rigid flanges 30 against the trachea for extended periods.

Figure 3:
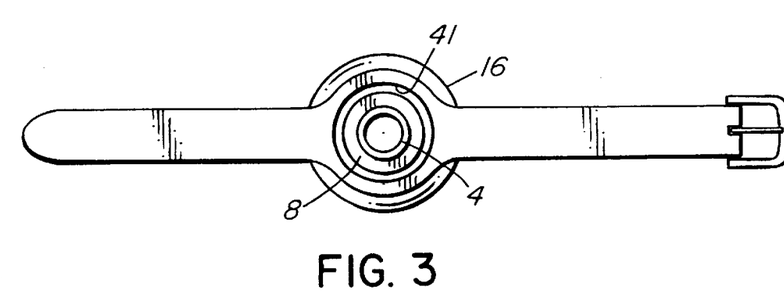
FIG. 3 is a detail view of the retaining strap for holding the tube of the first embodiment in place.

When inserted into the trachea, tube 4 has a tendency to move outwardly and must be restrained from doing so. In the apparatus of the present invention, a retainer member 39 is preferably provided adjacent outer end 8 of tube 4 to prevent excess outward movement of tube 4. FIG. 3 shows retainer 39 in the form of a strap and buckle connectable about the neck of the subject. The strap includes a circular opening 41 dimensioned to permit free movement of outer end 8 of tube 4 therethrough while preventing passage of cuff 16. Therefore, abutting of cuff 16 against the strap serves to prevent excess outward movement of tube 4.

Figure 1A:
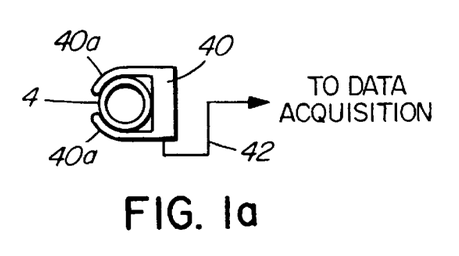
FIG. 1a is a detail view showing the manner of attachment of the sensor to the tube of FIG. 1.
Figure 9:
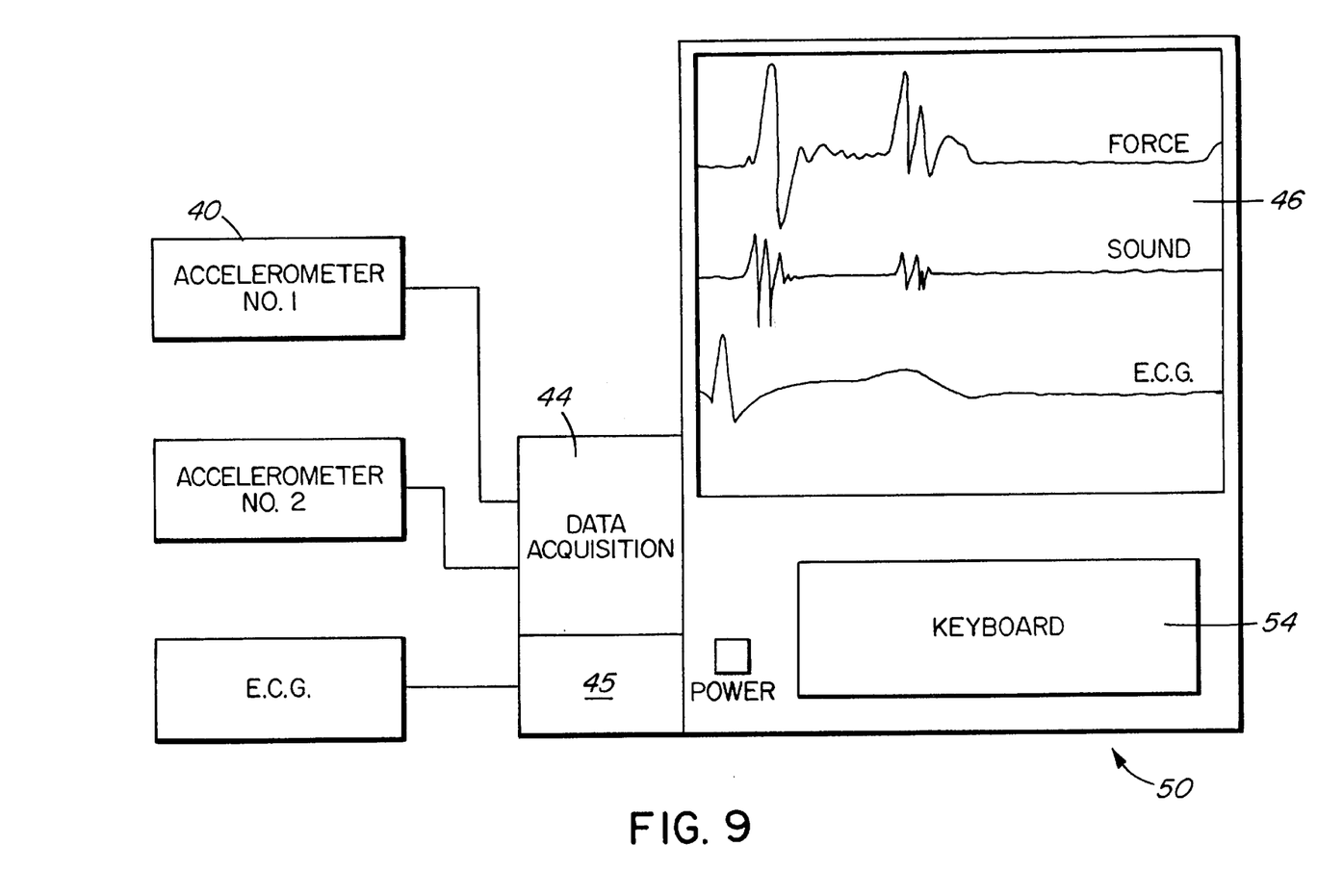
FIG. 9 is a schematic view of the display unit used with the apparatus of the present invention to show typical cardiac events and inputs from the sensors.

Movement of tube 4 is detected by sensor 40 attached to the outer end 8 of tube 4. As best shown in FIG. 1a, sensor 40 can be clipped to the tube via arms 40a to permit convenient interchange of sensors. In all cases, sensor 40 is selected to generate a signal indicative of movement of the tube and thus the trachea. Sensor 40 is preferably an accelerometer which senses the acceleration or velocity of tube 4. Alternatively, sensor 40 can be selected to measure displacement of tube 4. The signal generated by sensor 40 is sent via data line 42 to a data acquisition unit 44. The data acquisition unit includes a signal processing unit 45 to receive the signal from sensor 40 and generate a waveform signal characteristic of cardiac function. Signal processing unit 45 includes an amplifier to amplify the signal from the accelerometer and a digitizer to digitize the amplified signal. A signal analysis unit is then used to analyze the amplified signal and generate a waveform signal characteristic of cardiac function. The resulting waveform signal is displayed on a monitor 46 for ease of inspection. The data acquisition unit 44, signal processing unit 45 and display unit 46 are preferably organized into a control unit 50. Control unit 50 includes a computer with keyboard 55 running appropriate software to acquire, manipulate, store and display the data provided by sensor 40. As shown in FIG. 9, control unit 50 can also include inputs for additional sensor data and electrocardiogram (ECG) readings for simultaneous display on monitor 46 for comparison purposes.

In use, tube 4 is lubricated and manipulated according to standard procedures of intubation to insert the tube through the mouth of the user into the trachea with cuffs 14 and 16 collapsed and flanges 30 in the folded position. Cuffs 14 and 16 are then inflated using syringes 18 and 20. Cuff 16 is located in the mouth and cuff 14 seals the airway between the tube and trachea. Together the cuffs co-operate to suspend tube 4 within the trachea for free vibratory movement in response to movement of the trachea. Flanges 30 are moved to the expanded position to contact the trachea and lock the tube and trachea together so that tube 4 transmits any movement of the trachea due to the heart's motion. Movement of tube 4 is sensed by sensor 40 clipped to the outer end of the tube. Sensor 40 is used to generate a waveform signal based on movement of the tube which is used to determine cardiac function. By inserting a tube directly into the trachea and using the tube itself to detect movement of the trachea, more accurate and reliable data regarding cardiac function can be acquired than was previously possible.

FIGS. 4–8 illustrate a second embodiment of the present invention in which the probe for insertion into the trachea comprises a tubular member 8 which is inserted through an endotracheal tube 50 to directly engage and monitor the movement of the carina region 52 where the trachea 54 bifurcates into the bronchial tubes 56.

Figure 4:
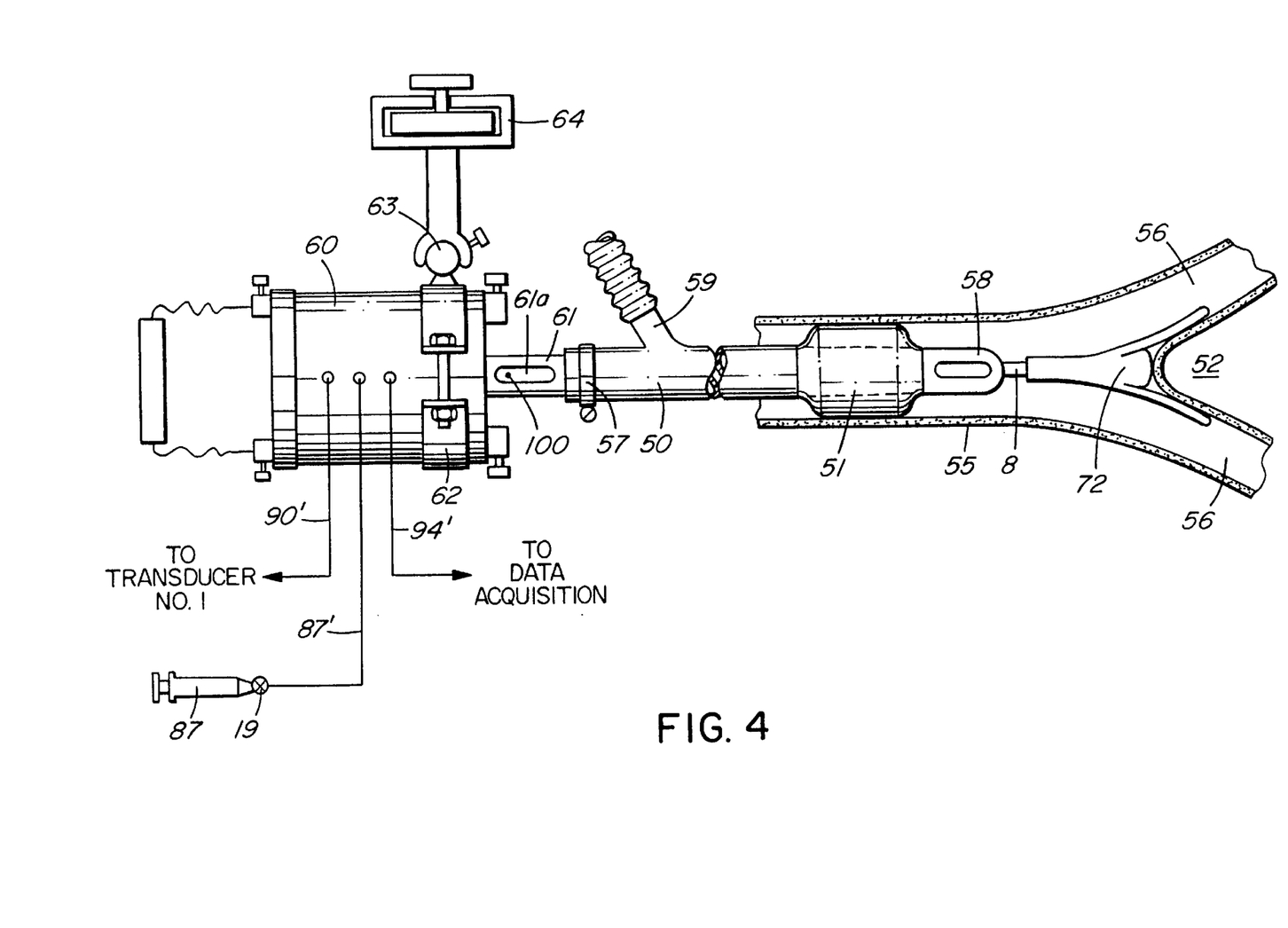
FIG. 4 shows a second embodiment of the apparatus of the present which relies on a probe inserted through an endotracheal tube to measure the movement of the carina region of the trachea.
Figure 5:
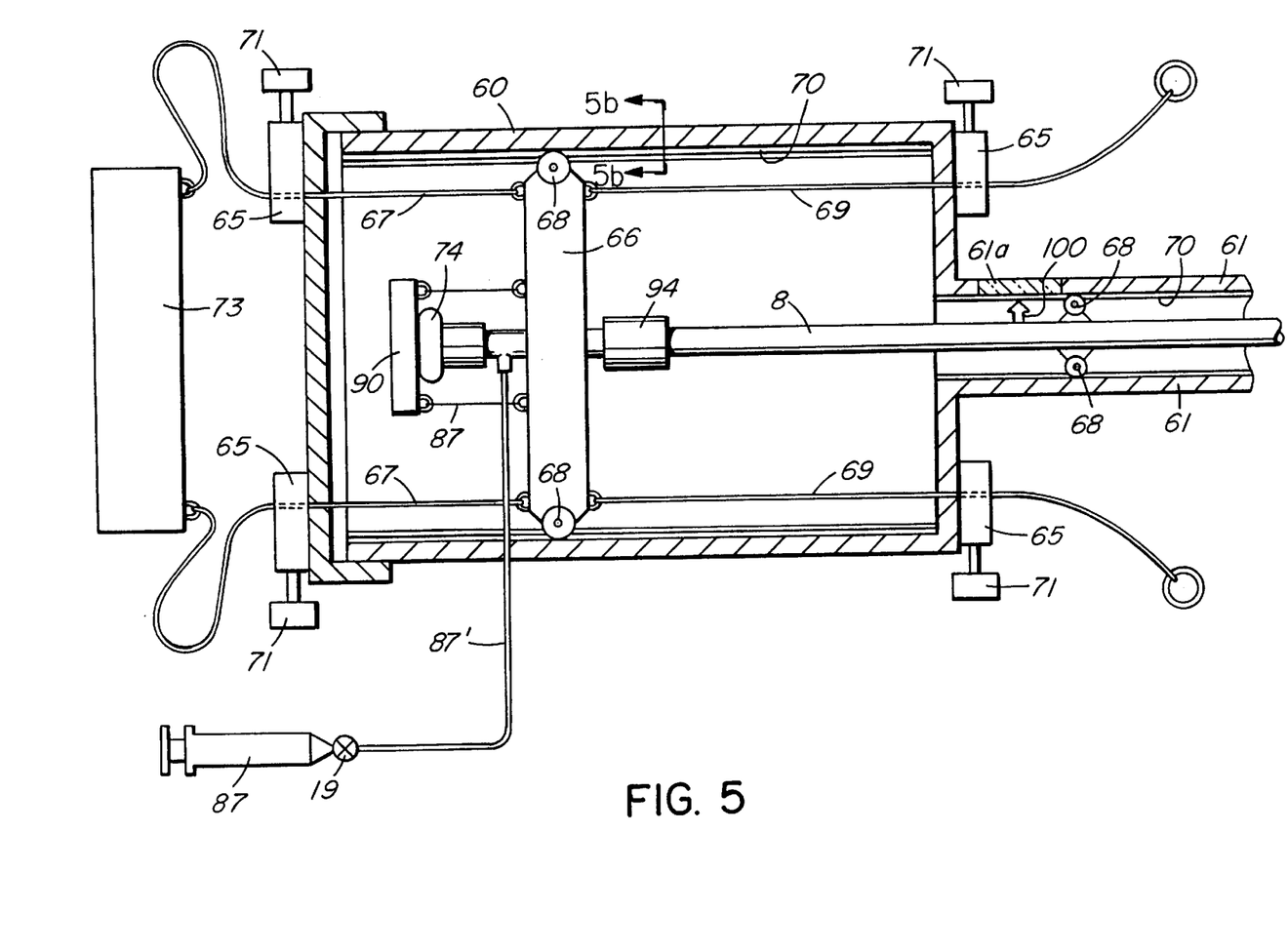
FIG. 5 is a detail section view through the mounting assembly that supports one end of the probe of the second embodiment via a movable carriage.

Referring to FIGS. 4 and 5, the apparatus of the second embodiment includes a mounting structure comprising a box housing 60 that supports one end of tubular member 8 to manipulate and manoeuvre the tubular member for insertion into the trachea of a subject via the mouth. Housing 60 includes tubular port 61 from which tubular member 8 protrudes. Housing 60 also includes an encircling clamp 62 and ball joint coupling 63 for connecting the housing to mounting bracket 64. Bracket 64 supports the entire apparatus and permits the apparatus to be oriented for ease of insertion of tubular member 8 into the trachea of a subject.

Figure 5A:
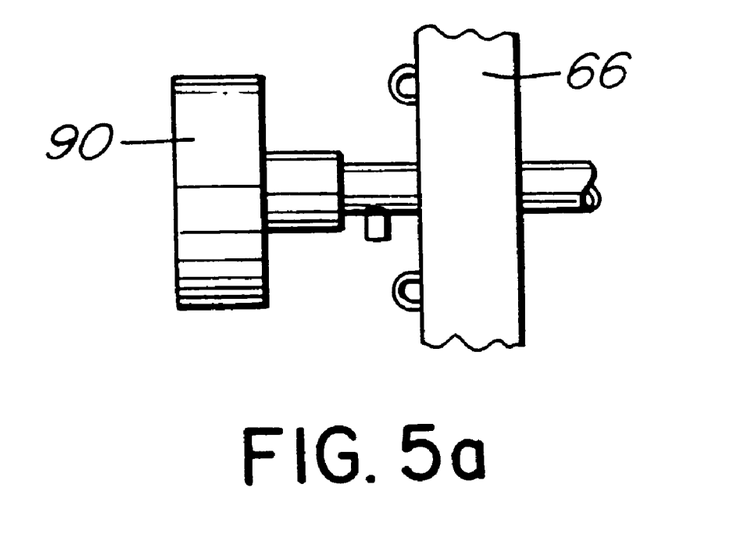
FIG. 5a is a detail view of an alternative sensor that can be used in apparatus of the second embodiment.
Figure 5B:
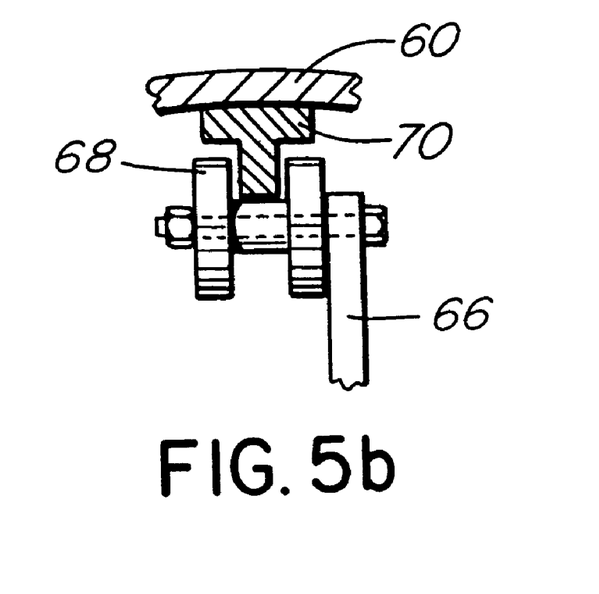
FIG. 5b is a detail view taken along line 5—5 in FIG. 5 showing the wheel arrangement that permits movement of the carriage.

FIG. 5 is a detail section view through housing 60. Housing 60 includes a movable carriage 66 to receive the outer end 74 of tubular member 8. Carriage 66 is movably supported by wheels 68 on rails 70 to permit adjustment of the position of tubular member 8 so that the member is biased against carina region 52 of the subject as will be explained in more detail below. To further support tubular member 8, wheels 68 are preferably mounted to the tubular member in the region of tubular port 61 to engage rails 70 mounted to the inner walls of the port. FIG. 5b is a section view taken along line 5—5 of FIG. 5 showing details of a preferred arrangement in which each wheel 68 includes a central channel to engage rail 70.

Tubular port 61 includes a window 61a to monitor the position of an indicator 100 fixedly mounted to tubular member 8. Indicator 100 in window 61a allows a user to determine the position of tubular member 8 within housing 60.

Figure 6:
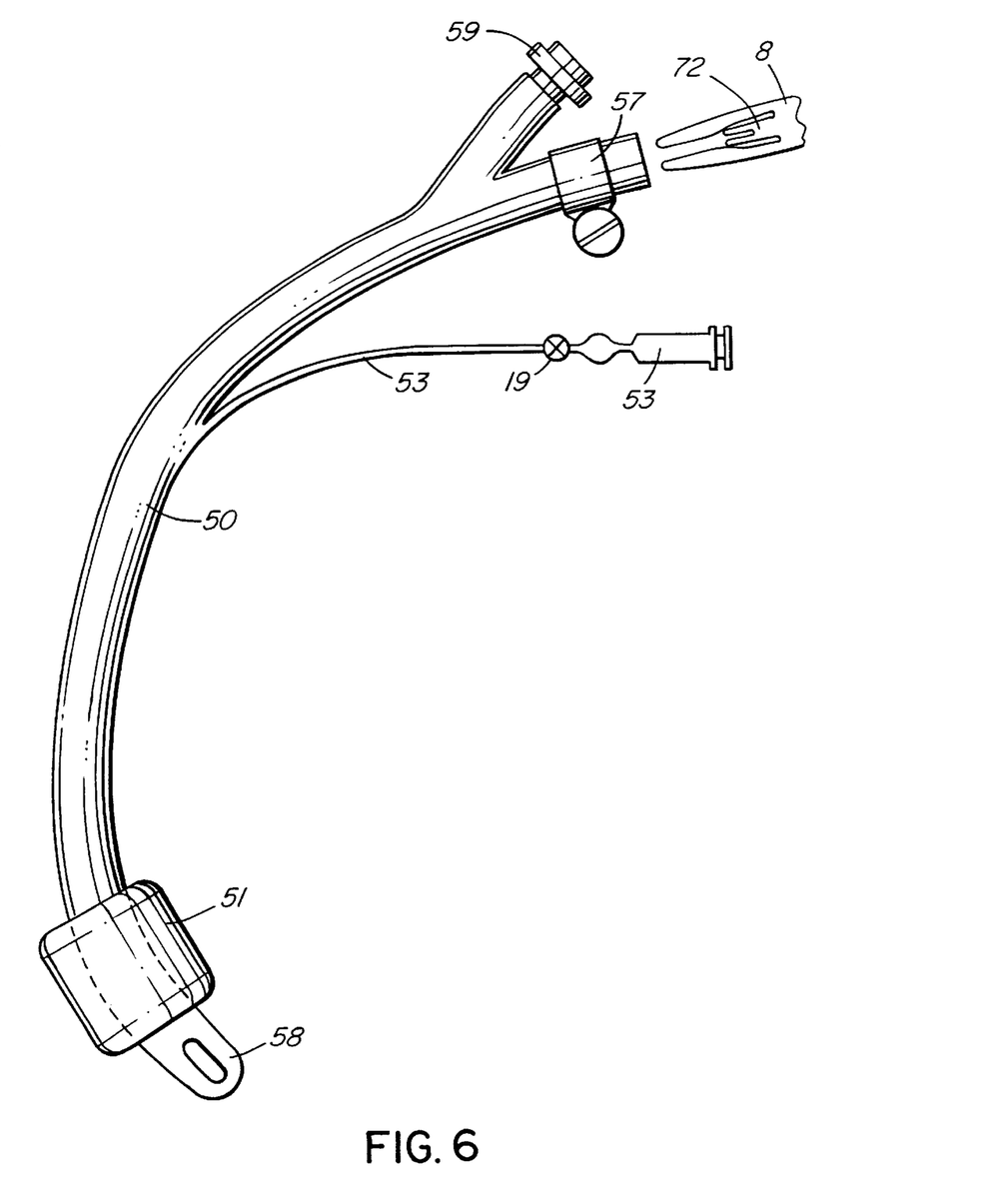
FIG. 6 shows an endotracheal tube used with the probe of the second embodiment.

Referring to FIG. 6, there is shown an endotracheal tube 50 used with the apparatus of the present embodiment. Tube 50 includes an inflatable cuff 15 that is controlled by syringe 53 via line 53' to retain tube 50 in the trachea of a subject. Tube 50 includes a main port 57 to receive end 72 of tubular member 8. Tubular member 8 is fed through the interior of endotracheal tube 50 via port 57 to protrude from end 58 for positioning against the carina. Endotracheal tube 50 also includes an auxiliary port 59 connectable to a ventilator for providing air to the subject through the interior of tube 50. As best shown in FIG. 4, port 57 of endotracheal tube 50 is releasably connectable to tubular port 61 of housing 60 to form a continuous passage to house tubular member 8 when inserted into the trachea of a subject.

As best shown in FIG. 5, the positioning of movable carriage 66 and thus the position of the tubular member in the trachea of the subject is preferably controlled by a spring biasing system. In the illustrated embodiment, the biasing system relies on spring loaded clamps 65 arranged in opposed pairs at each end of housing 60. Each clamp 65 controls a line connected to movable carriage 66. Fixed length lines 67 (preferably of nylon cord) extend from one side of carriage 66 while elastic lines 69 extend from the opposite side to exert a biasing force that tends to move the carriage and the attached tubular member 8 toward the subject. Lines 67 are connected to handle 73. Each clamp 65 includes a control knob 71 that is normally biased inwardly to grip and hold the line extending through the clamp. Pulling the control knob releases the clamp to allow movement of the lines. In use, the clamps controlling lines 67 are released and handle 73 is pulled to move carriage 66 and tubular member 8 to a predetermined position as shown by indicator 100 in port window 61a. Carriage 66 is moved against the return force exerted by stretching of elastic cords 69. The clamps for lines 67 are then engaged to hold the lines in place. This procedure locks the movable carriage 66 into a parked position for initial insertion of the tubular member into the trachea of a subject via endotracheal tube 50. After insertion of tubular member 8, the clamps 65 controlling lines 67 are released with the result that tubular member 8 mounted to carriage 66 will be biased against the carina of the subject by the tension force in stretched elastic lines 69. The clamps 65 controlling elastic lines 69 are provided to permit adjustment of the tension in the elastic lines.

Figure 7A:
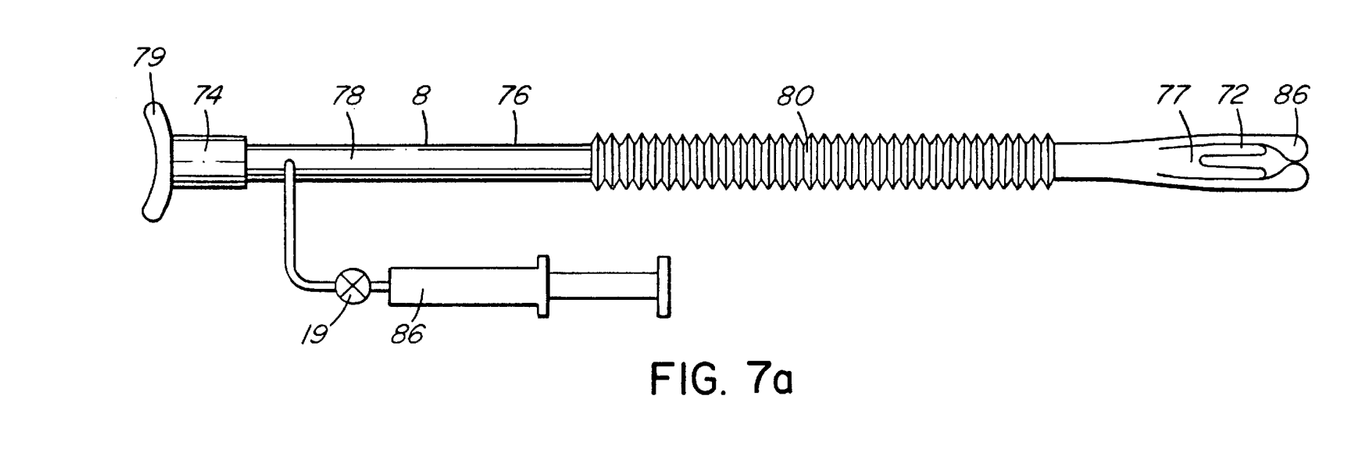
FIGS. 7a and 7b show the probe with an inner end having locating fingers in a collapsed position to facilitate insertion through the endotracheal tube and an extended position to locate the inner end on the carina region.
Figure 7B:
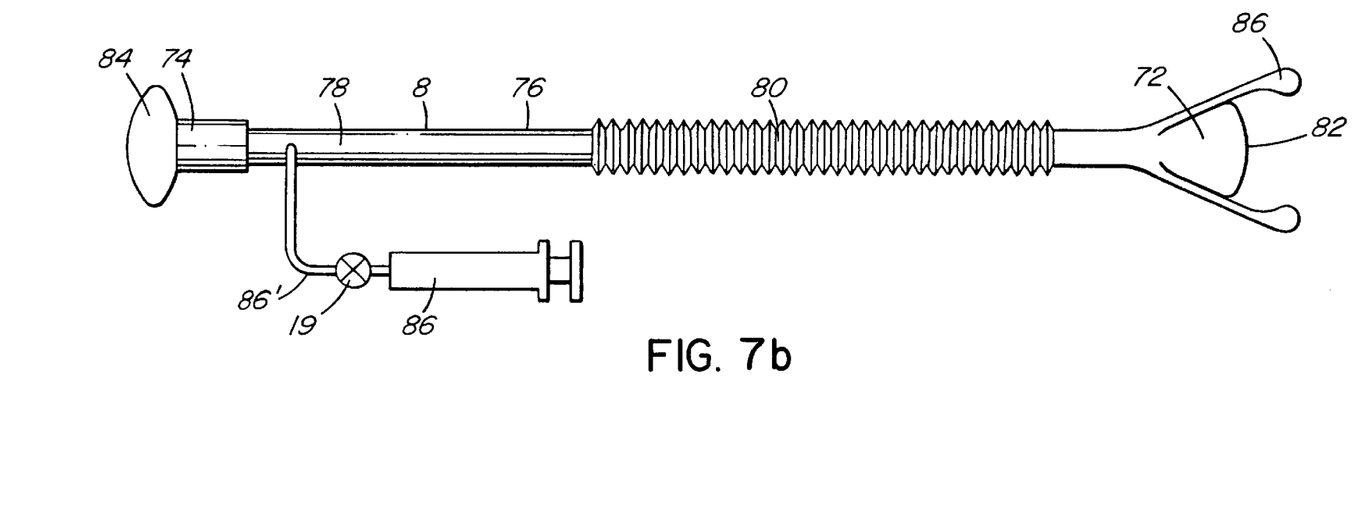

As best shown in FIGS. 7a and 7b, tubular member 8 comprises an inner end 72 adapted to protrude from the endotracheal tube 50 and engage against carina region 52, and outer end 74 supported in movable carriage 66 of housing 60. Tubular member 8 has substantially rigid side walls 76 defining a sealed interior filled with a fluid 78 communicating the inner and outer ends. Preferably, side walls 76 include a bendable region 80 formed with corrugations to accommodate curvature of the trachea.

Inner end 72 and outer end 74 of tubular member 8 include resilient surfaces 82 and 84, respectively, that communicate via the fluid in sealed interior 78. Movement of resilient surface 82 at inner end 72 due to movement of the carina region 52 is transmitted by fluid 78 to resilient surface 84 at outer end 74. To assist in locating inner end 72 of tubular member 8 on the carina region, collapsible locating fingers 86 are provided. Fingers 86 are movable between a collapsed position shown in FIG. 7a and a extended position shown in FIG. 7b. In the collapsed position, fingers 86 are aligned with the side walls of tubular member 8 to facilitate insertion through endotracheal tube 50 and the trachea. In the extended position, fingers 86 are positioned to engage the carina region to maintain resilient surface 82 on the carina region.

Fingers 86 are movable between the collapsed and extended positions by hydraulic pressure created by withdrawing fluid 78 from or injecting fluid 78 into the interior of tubular member 8. The inner and outer ends of tubular member 8 are formed as collapsible bulbs 77 and 79 that include resilient surfaces 82 and 84. A syringe 87 with check valve 19 communicates with the interior of tubular member 8 via line 87' to withdraw or inject fluid to collapse or inflate the bulbs. At inner end 72, bulb 77 acts to bias fingers 86 between the collapsed and extended positions.

As best shown in FIG. 5, resilient surface 84 of outer end 74 of tubular member 8 is positioned against sensor 90 which is mounted to carriage 66 by resilient lines 87. Any movement of resilient surface 82 at inner end 72 of member 8 is transmitted by fluid 78 to resilient surface 84 for detection by sensor 90. In FIG. 5, sensor 90 comprises an accelerometer to measure the acceleration and velocity of resilient surface 84 in response to movement of resilient surface 82 at the carina region. Alternatively, as shown in FIG. 5a, sensor 90 can be a pressure transducer mounted directly to the end of tubular member 8 to replace bulb 84 and to detect pressure changes at the inner end 74.

In the arrangement of the second embodiment, it is also possible to include an additional sensor 94 mounted to the rigid side walls of tubular member 8 to detect acoustic energy transmitted through the side walls of the tubular member by the beating heart. In this manner, the sounds associated with cardiac function can also be recorded.

Figure 8:
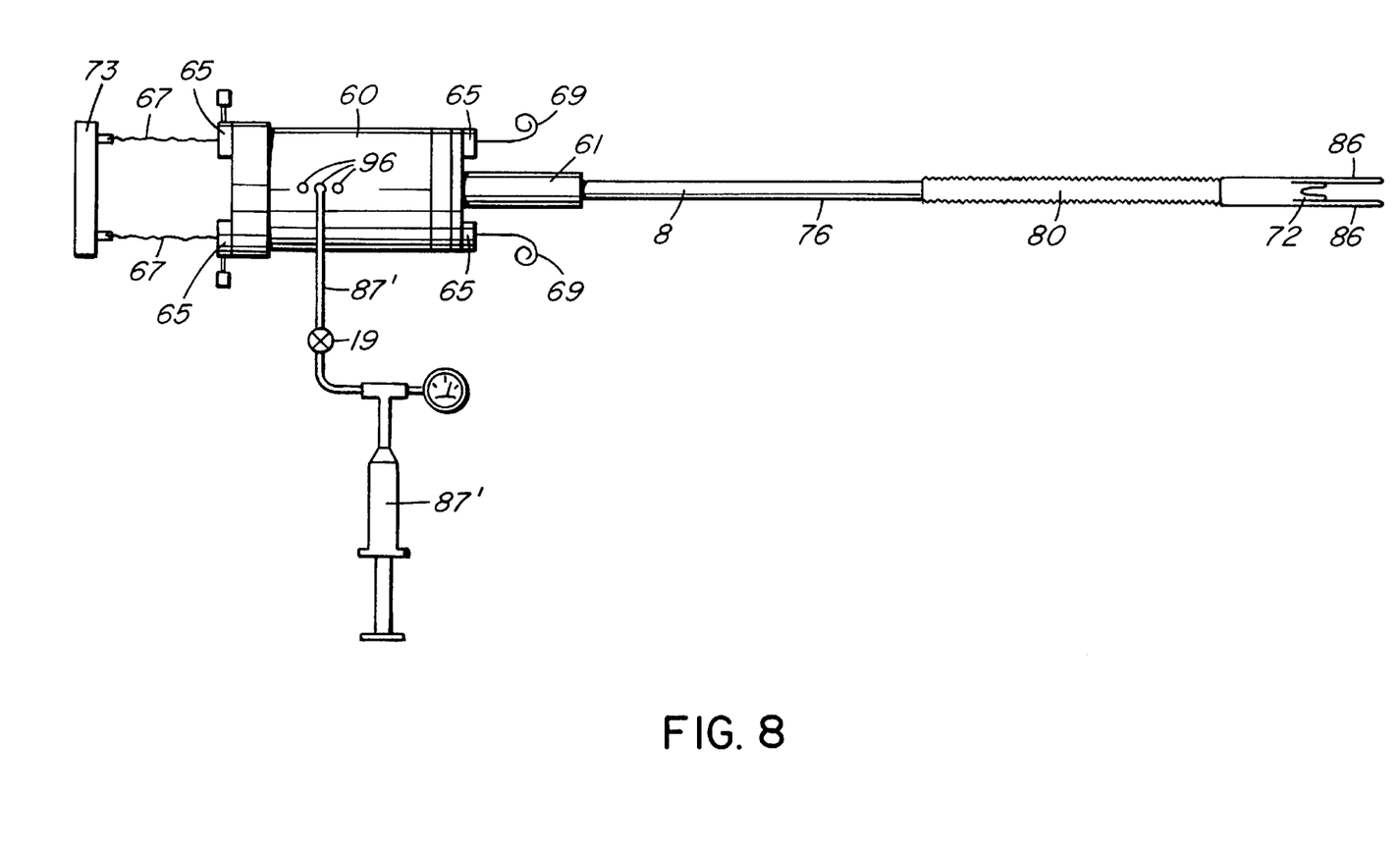
FIG. 8 shows the probe and mounting assembly of the second embodiment prior to insertion into the endotracheal tube of FIG. 6.

The various sensors 90 and 94 of the second embodiment are connectable via data lines 90' and 94' to the data acquisition unit shown in FIG. 9 for analysis and display of the collected data relating to cardiac function. As best shown in FIGS. 4 and 8, housing 60 is provided with ports 96 to permit syringe line 87' and data lines 90' and 94' to extend from the interior of housing 60 to the exterior. Syringe line 87' connects to syringe 87 via check valve 19.

Using the apparatus of the second embodiment involves lubricating endotracheal tube 50 with a water soluble gel and intubating the subject in a conventional manner. When cuff 51 is well within the trachea and within a few centimeters of the carina, the cuff is inflated by syringe 87. Tubular member 8 is positioned within housing 60 using handle 73. FIG. 8 shows the apparatus prior to insertion of tubular member 8 into endotracheal tube 50 with fingers 86 in the collapsed position. Tubular member 8 is inserted through endotracheal tube via port 55. The inner end 72 of tubular member 8 is pushed forward until the end exits the endotracheal tube about 2 cm at which point the endotracheal tube 50 is connected to tubular port 61 of housing 60. Fluid 78 is injected into tubular member 8 by syringe 87 via line 87' resulting in fingers 86 separating. Clamps 65 controlling lines 67 are slowly released and movable carriage 66 is moved by the biasing force of elastic lines 69 to carry tubular member 8 into engagement with the carina region. Resilient surface 82 of tubular member 8 abuts the carina while fingers 86 contact the sides of the carina region to assure proper positioning. Global movement of the heart is transmitted by the carina to the resilient surface 82. As the carina moves in response to the forces of the heart, resilient membrane 82 transmits its acceleration and deceleration through fluid 78 to resilient surface 84 at outer end 74. Accelerometer 90 is elastically attached and outputs to the data acquisition unit. An additional accelerometer sensor 94 having a higher frequency response outputs the acoustic energy received through the rigid walls 76 of tubular member 8. This sound energy is fed to the data acquisition system via data line 94'.

When using the apparatus or method of the present invention, certain body positions are preferable for optimal recording of cardiac functions as follows:
1) Head bent slightly towards the chest. This position frees the trachea for movement.
2) Diaphragm pushed upwards. This position forces the heart against the bronchus for better transmission.
3) Sitting Position with the feet placed up on a rail 4" higher than chair. This position compresses the diaphragm. The head is preferably bent towards the chest to free the trachea for movement.
4) Supine Position 5) On back with cushion under head inflated bag around abdomen with knees up.

6) Decubitus Position—legs folded against abdomen.

Although the present invention has been described in some detail by way of example for purposes of clarity and understanding, it will be apparent that certain changes and modifications may be practised within the scope of the appended claims.

I claim:

1. Apparatus to assess cardiac function in a subject comprising:
    a tube insertable into the mouth of a subject such that a first end extends into the trachea and a second end protrudes from the mouth;
    a flexible support extendable from the tube to suspend the tube within the trachea for movement of the tube along the longitudinal axis of the tube;
    a rigid anchor extendable from the tube to engage the trachea and transmit movement of the trachea due to cardiac function to the tube;
    a sensor to sense the movement of the tube and generate a signal indicative of the movement of the trachea; and
    a signal processing unit to receive the signal from the sensor and generate a waveform signal characteristic of the cardiac function.

2. Apparatus as claimed in claim 1 in which the flexible support comprises at least two spaced, inflatable cuffs extending about the tube, each cuff being inflatable from a collapsed position against the tube to an inflated position to engage the trachea.

3. Apparatus as claimed in claim 1 in which the tube has a passage to allow for the delivery of air to the subject when the tube is in place in the trachea.

4. Apparatus as claimed in claim 3 in which the second end of the tube is adapted to be connected to a ventilator unit.

5. Apparatus as claimed in claim 1 in which the sensor is an accelerometer positioned to sense the acceleration and velocity of the tube.

6. Apparatus as claimed in claim 1 in which the rigid anchor comprises a hinged flange pivotable between a folded position against the tube and a radially expanded position extending between the tube and the trachea.

7. Apparatus as claimed in claim 6 in which the hinged flange includes an inflatable bladder positioned between the tube and the flange such that inflation of the bladder moves the flange to the expanded position and deflation of the bladder moves the flange to the folded position.

8. Apparatus as claimed in claim 1 in which the signal processing unit includes:
    an amplifier to amplify the signal from the accelerometer;
    a digitizer to digitize the amplified signal;
    a signal analysis unit to analyze the amplified signal and generate the waveform signal characteristic of the cardiac function; and
    a display to show the waveform signal.

9. Apparatus as claimed in claim 1 including a retainer member attachable to the second end of the tube to assist in maintaining the position of the tube in a subject.

10. Apparatus as claimed in claim 9 in which the retainer member comprises a strap attachable to the tube adjacent the second end and extendable about the neck of the subject.

11. A method of assessing cardiac function in a subject comprising:
    supporting a tube in the trachea for movement with the trachea in response to cardiac function;
    sensing the movement of the tube;
    generating and displaying a waveform signal based on movement of the tube; and
    assessing the waveform signal to determine cardiac function.

12. A method as claimed in claim 11 in which the step of supporting a tube in the trachea includes the steps of:
    inserting a tube into the mouth of the subject to extend into the trachea;
    suspending the tube within the trachea for movement of the tube along the longitudinal axis of the tube;
    connecting the tube to the trachea such that movement of the trachea in response to cardiac function is transmitted to the tube.

13. A method as claimed in claim 12 in which the step of connecting the tube to the trachea involves providing anchors extendable from the tube to engage the trachea.

14. A method as claimed in claim 11 in which the step of sensing movement of the tube comprises measuring the acceleration, velocity or displacement of the tube by a sensor mounted to the tube.

15. A method as claimed in claim 11 in which the tube includes a passage to deliver air to the patient.

16. Apparatus to assess cardiac function in a subject comprising:
    a tube insertable and supportable in the trachea to transmit movement of the trachea in response to cardiac function to the tube;
    a sensor to sense the movement of the tube and generate a signal indicative of the movement of the trachea; and
    a signal processing unit to receive the signal from the sensor and generate a waveform signal characteristic of the cardiac function.

17. Apparatus as claimed in claim 16 in which the tube is insertable into the mouth of a subject such that a first end extends into the trachea and a second end protrudes from the mouth.

18. Apparatus as claimed in claim 16 including a flexible support extendable from the tube to engage the trachea and suspend the tube within the trachea for movement of the tube along the longitudinal axis of the tube.

19. Apparatus as claimed in claim 18 including a rigid anchor extendable from the tube to engage the trachea and transmit movement of the trachea in response to cardiac function to the tube.

20. Apparatus as claimed in claim 18 in which the flexible support comprises at least two spaced, inflatable cuffs extending about the tube, each cuff being inflatable from a collapsed position against the tube to an inflated position.

21. Apparatus as claimed in claim 17 in which the tube has a passage to allow for the delivery of air to the subject when the tube is in place in the trachea.

22. Apparatus as claimed in claim 17 in which the second end of the tube is adapted to be connected to a ventilator unit.

23. Apparatus as claimed in claim 16 in which the sensor is an accelerometer positioned to sense the acceleration and velocity of the tube.

24. Apparatus as claimed in claim 18 in which the rigid anchor comprises a hinged flange pivotable between a folded position against the tube and a radially expanded position extending between the tube and the trachea.

25. Apparatus as claimed in claim 24 in which the hinged flange includes an inflatable bladder positioned between the tube and the flange such that inflation of the bladder moves the flange to the expanded position and deflation of the bladder moves the flange to the folded position.

26. Apparatus as claimed in claim 16 in which the signal processing unit includes:
- an amplifier to amplify the signal from the accelerometer;
- a digitizer to digitize the amplified signal;
- a signal analysis unit to analyze the amplified signal and generate the waveform signal characteristic of the cardiac function; and
- a display to show the waveform signal.

27. Apparatus as claimed in claim 17 including a retainer member attachable to the second end of the tube to assist in maintaining the position of the tube in a subject.

28. Apparatus as claimed in claim 27 in which the retainer member comprises a strap attachable to the tube adjacent the second end and extendable about the neck of the subject.

29. Apparatus to assess cardiac function in a subject comprising:
- a probe insertable and supportable in the trachea to transmit movement of the trachea in response to cardiac function through the probe;
- a sensor to detect the transmitted movement of the trachea and generate a signal indicative of the movement of the trachea; and
- a signal processing unit to receive the signal from the sensor and generate a waveform signal characteristic of the cardiac function.

30. Apparatus as claimed in claim 29 in which the probe is a hollow tube having an internal passage to deliver air to the subject and whereby movement of the hollow tube serves to transmit the movement of the trachea.

31. Apparatus as claimed in claim 30 including a flexible support extendable from the tube to engage the trachea and suspend the tube within the trachea for movement of the tube along the longitudinal axis of the tube.

32. Apparatus as claimed in claim 30 including a rigid anchor extendable from the tube to engage the trachea and transmit movement of the trachea in response to cardiac function to the tube.

33. Apparatus as claimed in claim 31 in which the flexible support comprises at least two spaced, inflatable cuffs extending about the tube, each cuff being inflatable from a collapsed position against the tube to an inflated position with the trachea or mouth region of the subject.

34. Apparatus as claimed in claim 29 including a endotracheal tube for housing the probe.

35. Apparatus as claimed in claim 34 in which the probe comprises a tubular member having an inner end adapted to protrude from the endotracheal tube and engage against the carina region at which the trachea bifurcates into the lungs and an outer end supported in a mounting structure for positioning the inner end against the carina region.

36. Apparatus as claimed in claim 35 in which the tubular member has substantially rigid side walls defining a sealed interior filled with a fluid communicating the inner and outer ends.

37. Apparatus as claimed in claim 36 in which the side walls of the tubular member include a bendable region to accommodate curvature of the trachea.

38. Apparatus as claimed in claim 36 in which the inner and outer ends include resilient surfaces that communicate via the sealed interior whereby movement of the resilient surface at the inner end due to movement of the carina region is transmitted by the fluid to the resilient surface at the outer end.

39. Apparatus as claimed in claim 38 in which the inner end includes collapsible locating fingers movable between a collapsed position aligned with the side walls of the tubular member to facilitate insertion through the endotracheal tube and an extended position to grip the carina region to maintain the resilient surface at the inner end in engagement on the carina region.

40. Apparatus as claimed in claim 39 in which the collapsible fingers are moved between the collapsed and extended positions by withdrawing fluid from or injecting fluid into, respectively, the interior of the tubular member.

41. Apparatus as claimed in claim 39 including a syringe communicating with the interior of the tubular member to withdraw or inject fluid.

42. Apparatus as claimed in claim 38 in which the resilient surface at the outer end engages the sensor.

43. Apparatus as claimed in claim 42 in which the sensor comprises an accelerometer which detects acceleration of the resilient surface.

44. Apparatus as claimed in claim 42 in which the sensor comprises a pressure transducer which detects pressure changes at the resilient surface.

45. Apparatus as claimed in claim 42 including an acoustic sensor associated with the tubular member to detect acoustic energy transmitted through the side walls of the tubular member.

46. Apparatus as claimed in claim 38 in which the mounting structure includes a movable carriage to support the outer end of the tubular member for movement of the tubular member to bias the resilient surface at the inner end against the carina region.

47. A method of assessing cardiac function in a subject comprising:
- supporting a probe in the trachea to transmit movement of the trachea in response to cardiac function;
- sensing the movement transmitted by the probe;
- generating and displaying a waveform signal based on movement transmitted by the probe; and
- assessing the waveform signal to determine cardiac function.

48. A method as claimed in claim 47 in which the probe is a hollow tube having an internal passage to deliver air to the subject, and whereby movement of the hollow tube serves to transmit the movement of the trachea.

49. A method as claimed in claim 47 in which an endotracheal tube houses the probe and the probe comprises a tubular member having an inner end adapted to protrude from the endotracheal tube and engage against the carina region at which the trachea bifurcates into the lungs and an outer end supported in a mounting structure for positioning the inner end against the carina region.

\* \* \* \* \*